United States Patent
Basa et al.

(10) Patent No.: US 10,835,477 B2
(45) Date of Patent: *Nov. 17, 2020

(54) ORAL CARE COMPOSITIONS CONTAINING POLYETHYLENE GLYCOL FOR PHYSICAL STABILITY

(71) Applicant: The Procter & Gamble Company, Cincinnati, OH (US)

(72) Inventors: Swapna Basa, Beijing (CN); Ross Strand, Beijing (CN); Haiqiu Tang, Beijing (CN); Hongmei Yang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/634,949

(22) Filed: Apr. 14, 2015

(65) Prior Publication Data

US 2015/0328131 A1 Nov. 19, 2015

(51) Int. Cl.
| | |
|---|---|
| A61K 8/86 | (2006.01) |
| A61K 8/34 | (2006.01) |
| A61K 8/21 | (2006.01) |
| A61K 8/46 | (2006.01) |
| A61Q 11/00 | (2006.01) |
| A61K 8/19 | (2006.01) |
| A61K 8/24 | (2006.01) |

(52) U.S. Cl.
CPC .................. *A61K 8/86* (2013.01); *A61K 8/19* (2013.01); *A61K 8/21* (2013.01); *A61K 8/24* (2013.01); *A61K 8/34* (2013.01); *A61K 8/345* (2013.01); *A61K 8/463* (2013.01); *A61Q 11/00* (2013.01); *A61K 2800/28* (2013.01); *A61K 2800/30* (2013.01); *A61K 2800/52* (2013.01); *A61K 2800/591* (2013.01)

(58) Field of Classification Search
CPC . A61K 8/463; A61K 8/21; A61K 8/86; A61K 8/24; A61K 8/19; A61K 8/345; A61K 8/34; A61K 2800/28; A61K 2800/52; A61K 2800/30; A61K 2800/591; A61Q 11/00

See application file for complete search history.

(56) References Cited

U.S. PATENT DOCUMENTS

| | | | |
|---|---|---|---|
| 3,119,743 A | 1/1964 | Yngve | |
| 4,046,872 A | 9/1977 | Mitchell et al. | |
| 4,283,385 A | 8/1981 | Dhabhar et al. | |
| 4,357,313 A * | 11/1982 | Harvey | ........... A61K 8/345 424/49 |
| 4,565,691 A | 1/1986 | Jackson | |
| 4,574,081 A | 3/1986 | Shymon | |
| 4,678,662 A | 7/1987 | Chan | |
| 4,701,319 A | 10/1987 | Woo | |
| 4,828,849 A | 5/1989 | Lynch et al. | |
| 5,939,052 A | 8/1999 | White, Jr. et al. | |
| 6,106,811 A | 8/2000 | Gibbs | |
| 6,159,446 A | 12/2000 | Randive et al. | |
| 6,696,045 B2 | 2/2004 | Yue et al. | |
| 6,759,876 B2 | 7/2004 | Inoue et al. | |
| 6,855,325 B1 | 2/2005 | Yvin et al. | |
| 7,648,363 B2 | 1/2010 | Oniki et al. | |
| 8,007,771 B2 | 8/2011 | Ramji et al. | |
| 2002/0001569 A1 | 1/2002 | Dromard | |
| 2003/0072721 A1 | 4/2003 | Riley et al. | |
| 2003/0095931 A1 | 5/2003 | Stier | |
| 2004/0062723 A1 | 4/2004 | Zaidel et al. | |
| 2004/0120902 A1 | 6/2004 | Wernett et al. | |
| 2004/0131560 A1 | 7/2004 | Corcoran et al. | |
| 2006/0134020 A1 | 6/2006 | Robinson et al. | |
| 2006/0159631 A1 | 7/2006 | Buch et al. | |
| 2007/0231278 A1 | 10/2007 | Lee et al. | |
| 2008/0230298 A1 | 9/2008 | Buch et al. | |
| 2009/0136584 A1 | 5/2009 | Hosoya et al. | |
| 2009/0269287 A1 | 10/2009 | Berta | |
| 2010/0086498 A1* | 4/2010 | Haught | ........... A61K 8/19 424/49 |
| 2012/0189561 A1 | 7/2012 | Randive et al. | |
| 2013/0064779 A1 | 3/2013 | Yamane et al. | |
| 2013/0280182 A1 | 10/2013 | Burgess et al. | |
| 2013/0344120 A1 | 12/2013 | Scott et al. | |
| 2014/0314690 A1 | 10/2014 | Fisher et al. | |

FOREIGN PATENT DOCUMENTS

| | | |
|---|---|---|
| CN | 101690699 A | 4/2010 |
| CN | 102284795 A | 12/2011 |
| CN | 103110548 A | 5/2013 |
| CN | 102283794 B | 7/2013 |

(Continued)

OTHER PUBLICATIONS

Pearce, et al. "The Effect of pH, Temperature and Plaque Thickness on the Hydrolysis of Monofluorophosphate in Experimental Dental Plaque", Caries Research, vol. 37, pp. 178-184, Feb. 1, 2003.
PCT/CN2014/077427 International Search Report and Written Opinion dated Feb. 17, 2016.
PCT/CN2014/077536 International Search Report and Written Opinion dated May 15, 2014.
PCT/CN2015/077634 International Search Report and Written Opinion dated Jul. 22, 2015.
PCT/CN2015/077634 Supplementary International Search Report and Written Opinion dated Feb. 26, 2016.
PCT/CN2015/077636 International Search Report and Written Opinion.

(Continued)

*Primary Examiner* — Lezah Roberts
(74) *Attorney, Agent, or Firm* — Parker D. McCrary; James E. Oehlenschlager; Alexandra S. Anoff

(57) ABSTRACT

Oral care compositions having polyethylene glycol are more phase stable, particularly with certain flavorants that have a specified range of Dielectric Constant and/or water number and/or C log P value.

11 Claims, 8 Drawing Sheets

(56) References Cited

FOREIGN PATENT DOCUMENTS

| CN | 103550102 A | 2/2014 |
|---|---|---|
| EP | 2057978 A1 | 5/2009 |
| KR | 2002/0054045 A | 7/2002 |
| KR | 2012/0042399 A | 5/2012 |
| WO | WO1998022079 A1 | 5/1998 |
| WO | WO2005058364 A1 | 2/2006 |
| WO | WO2007076001 A3 | 9/2007 |
| WO | WO 2007/122146 A1 | 11/2007 |
| WO | WO2008041055 A1 | 4/2008 |
| WO | WO2008005548 A3 | 7/2009 |
| WO | WO2010114546 A1 | 10/2010 |
| WO | WO2011031807 A3 | 3/2011 |
| WO | WO2011157497 A1 | 12/2011 |
| WO | WO2013034421 A1 | 3/2013 |
| WO | WO2013094312 A1 | 6/2013 |
| WO | WO2015094152 A1 | 6/2016 |
| WO | WO2015094154 A1 | 6/2016 |

OTHER PUBLICATIONS

EP 15793035 upplementary European Search Report dated Oct. 20, 2017.
All Office Actions, U.S. Pat. No. 9,687,427.
All Office Actions, U.S. Appl. No. 14/633,389.
All Office Actions, U.S. Pat. No. 9,498,416.
All Office Actions, U.S. Appl. No. 15/294,855.
All Office Actions, U.S. Appl. No. 14/634,969.
All Office Actions, U.S. Appl. No. 14/635,234.
All Office Actions, U.S. Appl. No. 14/700,182.
All Office Actions, U.S. Appl. No. 14/830,815.
All Office Actions, U.S. Appl. No. 14/634,993.
All Office Actions, U.S. Appl. No. 14/830,831.
All Office Actions, U.S. Appl. No. 14/634,949.
All Office Actions, U.S. Pat. No. 9,364,419.
All Office Actions, U.S. Appl. No. 15/150,486.
All Office Actions, U.S. Appl. No. 14/682,146.
All Office Actions, U.S. Appl. No. 14/700,196.
All Office Actions, U.S. Appl. No. 14/830,839.
All Office Actions, U.S. Appl. No. 14/736,352.
PCT/CN2014/077527 Supplementary International Search Report and Written Opinion dated Jul. 27, 2016.
PCT/CN2014/077527 International Search Report and Written Opinion dated Feb. 27, 2015.
All Office Actions, U.S. Appl. No. 14/682,141.
PCT/CN2014/077531 International Search Report and Written Opinion dated Feb. 17, 2015.
PCT/CN2014/077531 Supplementary International Search Report and Written Opinion dated Oct. 8, 2016.
PCT/CN2014/077533 International Search Report and Written Opinion dated Feb. 27, 2015.
PCT/CN2014/077533 Supplementary International Search Report and Written Opinion dated Aug. 8, 2016.

\* cited by examiner

| Flavor Ingredient | Chemical name | CAS No. | CLogP | High Polarity "T" (Wt%) | Medium Polarity "A" (Wt%) | Medium Polarity "W" (Wt%) | Low Polarity "C" (Wt%) |
|---|---|---|---|---|---|---|---|
| Propylene Glycol | Propane-1,2-diol | 57-55-6 | -1.1 | 19.1% | | | |
| Methyl Salicylate | methyl 2-hydroxybenzoate | 000119-36-8 | 2.08 | | | 20% | |
| Geranial | (E)-3,7-Dimethyl-2,6-octadienal | 141-27-5 | 2.33 | | | | 1% |
| trans-Anethole | 1-Methoxy-4-((E)-1-propenyl)-benzene | 004180-23-8 | 2.43 | | 11% | 4% | 10% |
| Linalool | 2,6-Dimethyl-2,7-octadien-6-ol | 78-70-6 | 2.44 | 0.86% | | | |
| Carvone | 6,8-p-Menthadien-2-one | 002244-16-8 | 2.47 | | | 4% | 2% |
| cis-Jasmone | 3-methyl-2-[(Z)-pent-2-enyl]cyclopent-2-en-1-one | 488-10-8 | 2.81 | 0.86% | | | |
| l-Menthone | (2S,5R)-5-methyl-2-propan-2-ylcyclohexan-1-one | 014073-97-3 | 3.03 | | 11.5% | 3% | 2% |
| Menthone | 5-methyl-2-propan-2-ylcyclohexan-1-one | 89-80-5 | 3.03 | | 5.6% | | |

Fig. 1A

| Flavor Ingredient | Chemical name | CAS No. | CLogP | High Polarity "T" (Wt%) | Medium Polarity "A" (Wt%) | Medium Polarity "W" (Wt%) | Low Polarity "C" (Wt%) |
|---|---|---|---|---|---|---|---|
| L-Menthol | (1R,2S,5R)-5-methyl-2-propan-2-ylcyclohexan-1-ol | 2216-51-5 | 3.06 | 60% | 51% | 56% | 4% |
| (+)-Neomenthol | (1S,2S,5R)-5-methyl-2-propan-2-ylcyclohexan-1-ol | 3623-51-6 | 3.06 | | 0.5% | | |
| Eucalyptol | 4,7,7-trimethyl-8-oxabicyclo[2.2.2]octane | 470-82-6 | 3.15 | 10.44% | 14% | 4% | |
| WS-3 | N-ethyl-5-methyl-2-propan-2-ylcyclohexane-1-carboxamide | 39711-79-0 | 3.24 | 4.0% | | 4% | |
| trans-3-Hexenyl iso-Valerate | hex-3-enyl 3-methylbutanoate | 10032-11-8 | 3.67 | | 0.3% | | |
| dl-Menthyl Acetate | (5-methyl-2-propan-2-ylcyclohexyl) acetate | 016409-45-3 | 3.78 | | 2% | | |

Fig. 1B

| Flavor Ingredient | Chemical name | CAS No. | CLogP | High Polarity "T" (Wt%) | Medium Polarity "A" (Wt%) | Medium Polarity "W" (Wt%) | Low Polarity "C" (Wt%) |
|---|---|---|---|---|---|---|---|
| beta-Pinene | 7,7-dimethyl-4-methylidenebicyclo[3.1.1]heptane | 18172-67-3 127-91-3 | 4.26 | | | | 9% |
| d-Limonene | 1-methyl-4-prop-1-en-2-ylcyclohexene | 5989-27-5 | 4.38 | | | 3% | 56% |
| alpha-Pinene | 4,7,7-trimethylbicyclo[3.1.1]hept-3-ene | 7785-70-8 | 4.46 | | | | 2% |
| gamma-Terpinene | 1-methyl-4-propan-2-ylcyclohexa-1,4-diene | 99-85-4 | 4.67 | | | | 7% |
| alpha-Terpinolene | 1-Methyl-4-(1-methylethylidene)-cyclohexene | 586-62-9 | 4.71 | | | | 1% |
| | | Weight Percentage Total: | | 95.3% | 96% | 98% | 94% |

Fig. 1C

| Components (wt%): | Ex.1 | Ex.2 | Ex.3 | Ex.4 | Ex.5 | Ex.6 | Ex.7 | Ex.8 | Ex.9 | Ex.10 | Ex.11 | Ex.12 | Ex.13 | Ex.14 | Ex.15 |
|---|---|---|---|---|---|---|---|---|---|---|---|---|---|---|---|
| USP Water | 59.05 | 58.05 | 58.25 | 58.55 | 57.55 | 59.05 | 58.05 | 58.25 | 58.55 | 57.55 | 59.05 | 58.05 | 58.25 | 58.55 | 57.55 |
| Calcium Carbonate | 32 | 32 | 32 | 32 | 32 | 32 | 32 | 32 | 32 | 32 | 32 | 32 | 32 | 32 | 32 |
| Silica Thickening | 2.6 | 2.6 | 2.6 | 2.6 | 2.6 | 2.6 | 2.6 | 2.6 | 2.6 | 2.6 | 2.6 | 2.6 | 2.6 | 2.6 | 2.6 |
| Carrageenan | 1.2 | 1.2 | 1.2 | 1.2 | 1.2 | 1.2 | 1.2 | 1.2 | 1.2 | 1.2 | 1.2 | 1.2 | 1.2 | 1.2 | 1.2 |
| Sodium Monoflourophosphate | 1.1 | 1.1 | 1.1 | 1.1 | 1.1 | 1.1 | 1.1 | 1.1 | 1.1 | 1.1 | 1.1 | 1.1 | 1.1 | 1.1 | 1.1 |
| Sodium CMC | 0.9 | 0.9 | 0.9 | 0.9 | 0.9 | 0.9 | 0.9 | 0.9 | 0.9 | 0.9 | 0.9 | 0.9 | 0.9 | 0.9 | 0.9 |
| tetraSodium pyrophosphate | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 |
| Sodium Lauryl Sulfate | 1.1 | 2.1 | 1.6 | 1.1 | 2.1 | 1.1 | 2.1 | 1.6 | 1.1 | 2.1 | 1.1 | 2.1 | 1.6 | 1.1 | 2.1 |
| Low Polarity Flavorant | 0.7 | 0.7 | 1 | 1.2 | 1.2 | - | - | - | - | - | - | - | - | - | - |
| Medium Polarity Flavorant | - | - | - | - | - | 0.7 | 0.7 | 1 | 1.2 | 1.2 | - | - | - | - | - |
| High Polarity Flavorant | - | - | - | - | - | - | - | - | - | - | 0.7 | 0.7 | 1 | 1.1 | 1.2 |
| Tribasic Sodium Phosphate | 0.42 | 0.42 | 0.42 | 0.42 | 0.42 | 0.42 | 0.42 | 0.42 | 0.42 | 0.42 | 0.42 | 0.42 | 0.42 | 0.42 | 0.42 |
| Saccharin Sodium, USP | 0.25 | 0.25 | 0.25 | 0.25 | 0.25 | 0.25 | 0.25 | 0.25 | 0.25 | 0.25 | 0.25 | 0.25 | 0.25 | 0.25 | 0.25 |
| Sodium Phosphate Monobasic Monohydrate | 0.08 | 0.08 | 0.08 | 0.08 | 0.08 | 0.08 | 0.08 | 0.08 | 0.08 | 0.08 | 0.08 | 0.08 | 0.08 | 0.08 | 0.08 |

Fig. 2A

| Ingredients (wt%): | Examples: STABILITY FOR SIX MONTHS UNDER AMBIENT CONDITIONS ("+" is stable; "-" is unstable) | | | | | | | | | | | | | | |
|---|---|---|---|---|---|---|---|---|---|---|---|---|---|---|---|
| | Ex.1 | Ex.2 | Ex.3 | Ex.4 | Ex.5 | Ex.6 | Ex.7 | Ex.8 | Ex.9 | Ex.10 | Ex.11 | Ex.12 | Ex.13 | Ex.14 | Ex.15 |
| Control (i.e., without PEG.) | - | - | - | - | - | - | - | - | - | - | - | - | - | - | - |
| PEG 300 (2%) (in lieu of USP water) | + | + | + | - | + | + | - | + | + | + | + | - | - | + | + |
| PEG 400 (2%) | + | + | + | + | + | + | + | + | + | + | + | + | + | + | + |
| PEG 600 (2%) | + | + | + | + | + | + | + | + | + | + | + | + | + | + | + |
| PEG 1000 (2%) | + | + | + | + | + | + | + | + | + | + | + | + | + | + | + |
| PEG 1300-1600 (2%) | + | + | + | + | + | + | + | + | + | + | + | + | + | + | + |

A "PEG1300-1600" is a mixture of 30 percent of PEG1300 by weight of the mixture and 70 percent of PEG1600 by weight of the mixture.

Fig. 2B

ORAL CARE COMPOSITIONS CONTAINING POLYETHYLENE GLYCOL FOR PHYSICAL STABILITY

CROSS REFERENCE TO RELATED APPLICATION

This application claims the benefit of Application No. CN2014/077533 filed May 15, 2014.

FIELD OF THE INVENTION

The present invention relates to oral care compositions, especially dentifrice.

BACKGROUND OF THE INVENTION

Dentifrice compositions are well known for dental and oral hygiene care. High water and high carbonate formulation chassis are a cost effective for many markets and consumers. However, this chassis sometimes has phase stability issues that often exacerbated when there are high temperatures and/or long distribution times (e.g., >5 months) such as in some developing markets. Flavor in dentifrice and in oral care compositions is critical for a user's experience and product acceptance. However, it was recently observed that same flavor components pose phase stability issues in these formulation chassis. There is a need to provide phase stable oral care formulations having consumer acceptable flavors.

SUMMARY OF THE INVENTION

The present invention is based on the observation that some flavor components pose toothpaste formulation phase stability challenges, particularly those formulation chassis having high water and high carbonate levels. The surprising solution to these phase stability challenges is the use of polyethylene glycol ("PEG"), especially PEG-9 to PEG-13. Without wishing to be bound by theory, the PEG stabilizes the emulsion of the toothpaste formulation by one or more of the following mechanisms: improving the solubility of the flavorant; increasing dissolution of surfactant (e.g., sodium lauryl sulfate); or decreasing critical micelle concentration of surfactant.

One advantage of the present invention is having high water and high carbonate toothpaste formulation that is compatible with a range of flavorants (to accommodate a variety of markets and consumer segments), especially those flavorants having medium to low polarity, especially low polarity. Without having low polarity flavorants or flavor ingredients available to formulation designers, the spectrum of flavors available to users would be limited.

Another advantage of the present invention is phase stable compositions. "Phase stability" means visually (i.e., to the unaided eye) having no liquid separated from the oral care composition (e.g., toothpaste) body over a defined period of time under ambient conditions. In other words, a phase stable composition will resist syneresis. In one embodiment, the oral care compositions of the present invention are phase stable after 4 months, preferably 6 months, at ambient conditions, alternatively are phase stable after 12 months at ambient conditions, alternatively even longer.

Yet another advantage of the present invention is that it contains a low amount of humectant (e.g., sorbitol, glycerol), alternatively substantially free or free of humectants. This minimizes cost and complexity to the formulation.

One aspect of the invention provides for a dentifrice composition comprising: (a) 20% to 75%, preferably 50% to 60% of water by weight of the composition; (b) 25% to 60%, preferably 27% to 47% of a calcium-containing abrasive by weight of the composition, preferably wherein the calcium-containing abrasive is calcium carbonate; (c) 0.1% to 15%, preferably from 1% to 10%, of a polyethylene glycol (PEG) by weight of the composition; and (d) 0.001% to 5% of a flavorant composition by weight of the dentifrice composition.

Another aspect of the invention provides for an oral care composition comprising: (a) 20% to 75%, preferably 50% to 60%, of water by weight of the composition; (b) 25% to 60%, preferably 27% to 47%, of a calcium-containing abrasive by weight of the composition, preferably wherein the calcium-containing abrasive is calcium carbonate; (c) 0.1% to 15%, of a polyethylene glycol (PEG) by weight of the composition, preferably wherein the PEG has an average molecular weight range from 200 Daltons to 1,000 Daltons; and (d) 0.001% to 5% of a flavorant composition by weight of the oral care composition.

Yet another aspect of the invention provides for a method of treating tooth enamel comprising the step of brushing teeth with a dentifrice composition of the present invention; or comprising the step of contacting teeth with an oral care composition of the present invention.

BRIEF DESCRIPTION OF THE DRAWINGS

FIGS. 1A, 1B and 1C identify known flavor ingredients and C log P value thereof of four flavorant compositions.

FIGS. 2A and 2B are a table detailing the components of formulation Examples 1-15.

Figure 3A:
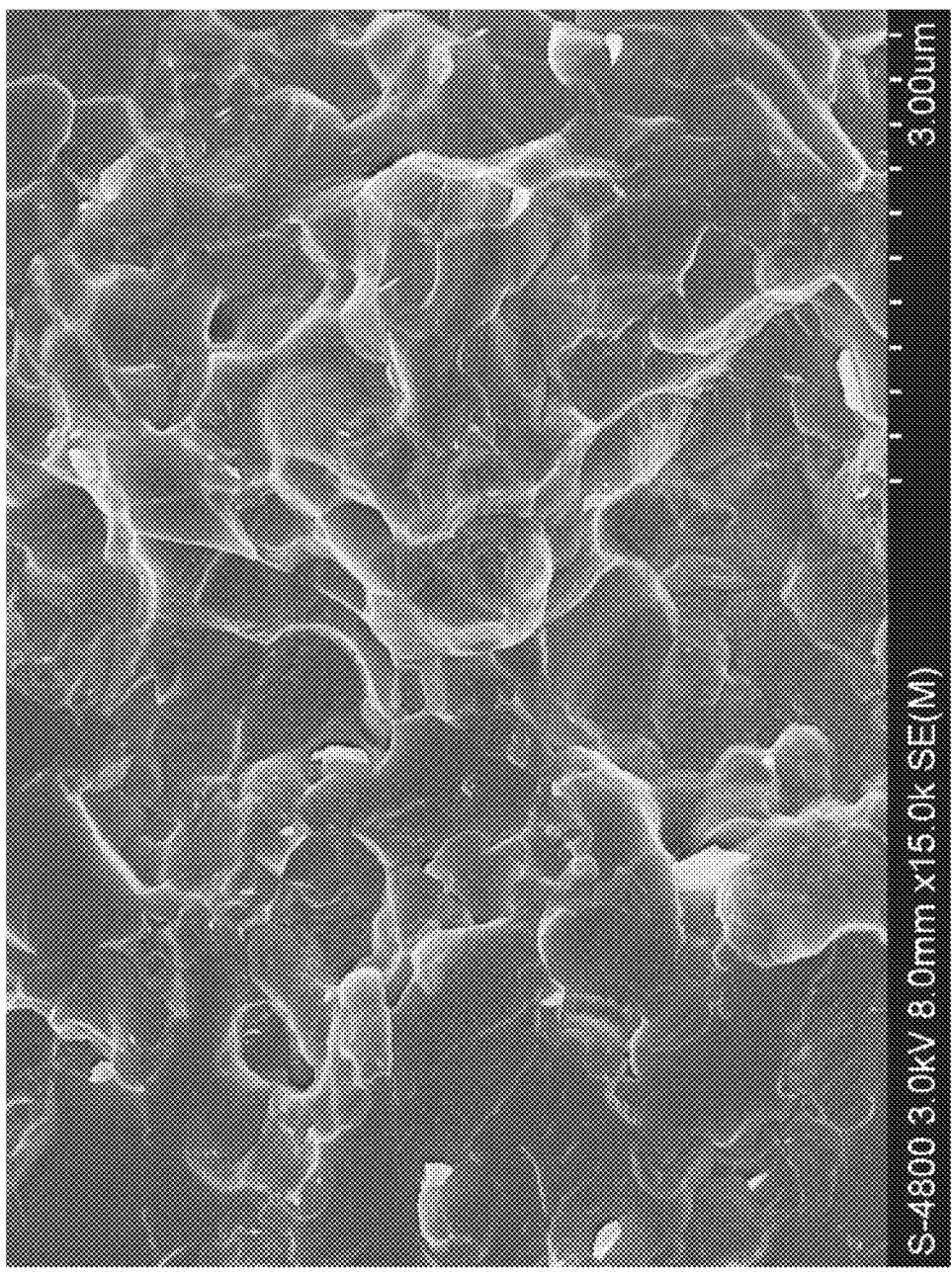
FIGS. 3A and 3B are Scanning Electron Microscopy (SEM) images of phase unstable compositions (FIG. 3A) and a phase stable composition (FIG. 3B).

While the specification concludes with claims that particularly point out and distinctly claim the invention, it is believed the present invention will be better understood from the following description.

DETAILED DESCRIPTION OF THE INVENTION

Definitions

The term "orally acceptable carrier" as used herein means a suitable vehicle or ingredient, which can be used to form and/or apply the present compositions to the oral cavity in a safe and effective manner.

The term "comprising" as used herein means that steps and ingredients other than those specifically mentioned can be added. This term encompasses the terms "consisting of" and "consisting essentially of" The compositions of the present invention can comprise, consist of, and consist essentially of the essential elements and limitations of the invention described herein, as well as any of the additional or optional ingredients, components, steps, or limitations described herein.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one embodiment, "effective amount"

means at least 0.01% of the material, by weight of the composition, alternatively at least 0.1%.

The term "oral composition" as used herein means a product that in the ordinary course of usage is retained in the oral cavity for a time sufficient to contact some or all of the dental surfaces and/or oral tissues for purposes of oral activity. In one embodiment, the composition is an "oral care composition" meaning that the composition provides a benefit when used in the oral cavity. The oral composition of the present invention may be in various forms including toothpaste, dentifrice, tooth gel, tooth powders, tablets, rinse, sub gingival gel, foam, mousse, chewing gum, lipstick, sponge, floss, prophy paste, petrolatum gel, or denture product. In one embodiment, the oral composition is in the form of a paste or gel. In another embodiment, the oral composition is in the form of a dentifrice. The oral composition may also be incorporated onto strips or films for direct application or attachment to oral surfaces, or incorporated into floss.

The term "dentifrice" as used herein means paste, gel, powder, tablets, or liquid formulations, unless otherwise specified, that are used to clean the surfaces of the oral cavity. The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Water

The compositions of the present invention comprise herein from 20% to 75%, by weight of the composition of total water. In one embodiment, the composition includes from 40% to 70%, alternatively from 45% to 65%, alternatively from 40% to 60%, alternatively from 50% to 70%, alternatively from 50% to 60%, alternatively from 45% to 55%, alternatively from 55% to 65%, alternatively from 50% to 60%, alternatively about 55%, alternatively combinations thereof, of water by weight of the composition. The water may be added to the formulation and/or may come into the composition from the inclusion of other ingredients. Preferably the water is USP water.

Calcium-Containing Abrasive

The compositions of the present invention comprise from 20% to 60% by weight of a calcium-containing abrasive, wherein the calcium-containing abrasive is selected from the group consisting of calcium carbonate, dicalcium phosphate, tricalcium phosphate, calcium orthophosphate, calcium metaphosphate, calcium polyphosphate, calcium oxyapatite, sodium carbonate, and combinations thereof. In a preferred embodiment, the composition comprises from 25% to 60%, more preferably from 25% to 50%, even more preferably from 25% to 40%, yet even more preferably from 26% to 39%, alternatively from 27% to 47%, alternatively from 27% to 37%, alternatively from 30% to 35%, alternatively from 30% to 34%, alternatively combinations thereof, of a calcium-containing abrasive by weight of the composition.

In one embodiment, the calcium-containing abrasive is calcium carbonate. In a preferred embodiment, the calcium-containing abrasive is selected from the group consisting of fine ground natural chalk, ground calcium carbonate, precipitated calcium carbonate, and combinations thereof.

Fine ground natural chalk (FGNC) is one of the more preferred calcium-containing abrasives useful in the present invention. It is obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling. One example of natural chalk is described in WO 03/030850 having a medium particle size of 1 to 15 µm and a BET surface area of 0.5 to 3 $m^2/g$. The natural calcium carbonate may have a particle size of 325 to 800 mesh, alternatively a mess selected from 325, 400 600, 800, or combinations thereof; alternatively the particle is from 0.1 to 30 microns, or from 0.1 to 20 microns, or from 5 to 20 microns.

In one embodiment, the composition of the present invention is free or substantially free of silicate.

PEG

The compositions of the present invention may comprise polyethylene glycol (PEG), of various weight percentages of the composition as well as various ranges of average molecular weights. In one aspect of the invention, the compositions have from 0.1% to 15%, preferably from 0.2% to 12%, more preferably from 0.3% to 10%, yet more preferably from 0.5% to 7%, alternatively from 1% to 5%, alternatively from 1% to 4%, alternatively from 1% to 2%, alternatively from 2% to 3%, alternatively from 4% to 5%, or combinations thereof, of PEG by weight of the composition. In another aspect of the invention, the PEG is one having a range of average molecular weight from 100 Daltons to 1600 Daltons, preferably from 200 to 1000, alternatively from 400 to 800, alternatively from 500 to 700 Daltons, alternatively combinations thereof. PEG is a water soluble linear polymer formed by the addition reaction of ethylene oxide to an ethylene glycol equivalent having the general formula: H—$(OCH_2CH_2)_n$—OH. One supplier of PEG is Dow Chemical Company under the brandname of CARBOWAX™.

Sweetener

The oral care compositions herein may include a sweetening agent. These include sweeteners such as saccharin, dextrose, sucrose, lactose, maltose, levulose, aspartame, sodium cyclamate, D-tryptophan, dihydrochalcones, acesulfame, sucralose, neotame, and mixtures thereof. Sweetening agents are generally used in oral compositions at levels of from 0.005% to 5%, by weight of the composition, alternatively 0.01% to 1%, alternatively from 0.1% to 0.5%, alternatively combinations thereof.

Fluoride Ion Source

The composition may include an effective amount of an anti-caries agent. In one embodiment, the anti-caries agent is a fluoride ion source. The fluoride ion may be present in an amount sufficient to give a fluoride ion concentration in the composition at 25° C., and/or in one embodiment can be used at levels of from about 0.0025% to about 5% by weight of the composition, alternatively from about 0.005% to about 2.0% by weight of the composition, to provide anti-caries effectiveness. Examples of suitable fluoride ion-yielding materials are disclosed in U.S. Pat. Nos. 3,535,421, and 3,678,154. Representative fluoride ion sources include: stannous fluoride, sodium fluoride, potassium fluoride, amine fluoride, sodium monofluorophosphate, and zinc fluoride. In one embodiment, the oral care composition contains a fluoride source selected from stannous fluoride, sodium fluoride, and mixtures thereof. In one embodiment, the fluoride ion source is sodium monofluorophosphate, and wherein the composition comprises 0.0025% to 2% of the sodium monofluorophosphate by weight of the composition, alternatively from 0.5% to 1.5%, alternatively from 0.6% to 1.7%, alternatively combinations thereof. In another embodiment, the composition comprises from 0.0025% to 2% of a fluoride ion source by weight of the composition.

pH

The pH of the oral composition may be greater than pH 7.8, or from 8 to 13, more preferably from 9 to 12, alternatively greater than 8, alternatively greater than 9, alternatively from 9 to 11, alternatively from 9 to 10, or combinations thereof.

A method for assessing pH of dentifrice is described. pH is measured by a pH Meter with Automatic Temperature Compensating (ATC) probe. The pH Meter is capable of reading to 0.001 pH unit. The pH electrode may be selected from one of the following (i) Orion Ross Sure-Flow combination: Glass body—VWR #34104-834/Orion #8172BN or VWR #10010-772/Orion #8172BNWP; Epoxy body—VWR #34104-830/Orion #8165BN or VWR #10010-770/Orion #8165BNWP; Semi-micro, epoxy body—VWR #34104-837/Orion #8175BN or VWR #10010-774/Orion #3175BNWP; or (ii) Orion PerpHect combination: VWR #34104-843/Orion #8203BN semi-micro, glass body; or (iii) suitable equivalent. The automatic temperature compensating probe is Fisher Scientific, Cat #13-620-16.

A 25% by weight slurry of dentifrice is prepared with deionized water, and thereafter is centrifuged for 10 minutes at 15000 rotations-per-minute using a SORVALL RC 28S centrifuge and SS-34 rotor (or equivalent gravitational force, at 24149 g force). The pH is assessed in supernatant after one minute or the taking reading is stabilized. After each pH assessment, the electrode is washed with deionized water. Any excess water is wiped with a laboratory grade tissue. When not in use, the electrode is kept immersed in a pH 7 buffer solution or an appropriate electrode storage solution.

pH Modifying Agent

The oral care compositions herein may include an effective amount of a pH modifying agent, alternatively wherein the pH modifying agent is a pH buffering agent. pH modifying agents, as used herein, refer to agents that can be used to adjust the pH of the dentifrice compositions to the above-identified pH range. pH modifying agents may include alkali metal hydroxides, ammonium hydroxide, organic ammonium compounds, carbonates, sesquicarbonates, borates, silicates, phosphates, imidazole, and mixtures thereof. Specific pH agents include monosodium phosphate (monobasic sodium phosphate), trisodium phosphate (sodium phosphate tribasic dodecahydrate or TSP), sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, orphosphoric acid. In one embodiment, from 0.01% to 3%, preferably from 0.1% to 1%, of TSP by weight of the composition, and 0.001% to 2%, preferably from 0.01% to 0.3% of monosodium phosphate by weight of the composition is used. Without wishing to be bound by theory, TSP and monosodium phosphate may also have calcium ion chelating activity and therefore provide some monofluorophosphate stabilization (in those formulations containing monofluorophospahte).

Anti-Calculus Agent

The oral care compositions may include an effective amount of an anti-calculus agent, which in one embodiment may be present from about 0.05% to about 50%, by weight of the oral care composition, alternatively from about 0.05% to about 25%, alternatively from about 0.1% to about 15%. Non-limiting examples include those described in US 2011/0104081 A1 at paragraph 64, and those described in US 2012/0014883 A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably 0.01% to 2%, more preferably from 0.1% to 1% of the pyrophosphate salt by weight of the composition. Without wishing to be bound by theory, TSPP may provide not only calcium chelating thereby mitigating plaque formation, but also provides the additional benefit of monofluorophosphate stabilization (in those formulations containing monofluorophosphate).

Surfactant

The compositions herein may include a surfactant. The surfactant may be selected from anionic, nonionic, amphoteric, zwitterionic, cationic surfactants, or mixtures thereof. The oral care composition may include a surfactant at a level of from about 0.1% to about 10%, from about 0.025% to about 9%, from about 0.05% to about 5%, from about 0.1% to about 2.5%, from about 0.5% to about 2%, or from about 0.1% to about 1% by weight of the total composition. Non-limiting examples of anionic surfactants may include those described at US 2012/0082630 A1 at paragraphs 32, 33, 34, and 35. Non-limiting examples of zwitterionic or amphoteric surfactants may include those described at US 2012/0082630 A1 at paragraph 36; cationic surfactants may include those described at paragraph 37 of the reference; and nonionic surfactants may include those described at paragraph 38 of the reference. In one embodiment, the composition comprises 0.1% to 5%, preferably 0.1% to 3%, alternatively from 0.3% to 3%, alternatively from 1.2% to 2.4%, alternatively from 1.2% to 1.8%, alternatively from 1.5% to 1.8%, alternatively combinations thereof, of the anionic surfactant sodium lauryl sulfate (SLS) by weight of the composition.

Thickening Agent

The oral care compositions herein may include one or more thickening agents. A thickening agent may be used in an amount from about 0.01% to about 15%, or from about 0.1% to about 10%, or from about 0.1% to about 5%, by weight of the composition. Non-limiting examples may include those described in US 2008/0081023 A1 at paragraphs 134 to 137, and the references cited therein.

In one embodiment, the composition comprises a linear sulfated polysaccharide as a thickening agent. Carrageenans or carrageenins are one example of a linear sulfated polysaccharide. Generally, carrageenans can vary based upon the degree of sulfation that includes: Kappa-carrageenan, Iota-carrageenan, and Lambda-carrageenan. Combinations of carrageenans can be used. In one embodiment, the composition contains from 0.1% to 3%, of a linear sulfated polysaccharides by weight of the composition, preferably from 0.5% to 2%, alternatively from 0.6% to 1.8%, alternatively combinations thereof. In one embodiment, Iota-carrageenan is used.

In one embodiment, the composition comprises a silica agent, preferably a thickening silica obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167). In one embodiment, the composition comprising from 0.5% to 5% by weight of the composition of a silica agent, preferably from 1% to 4%, alternatively from 1.5% to 3.5%, alternatively from 2% to 3%, alternatively from 2% to 5% alternatively from 1% to 3%, alternatively combinations thereof.

In one embodiment, the composition comprises a carboxymethyl cellulose ("CMC"). CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9 M3SF Aqualon™ TM9A; Aqualon™ TM12A). In one embodiment, the composition contains from 0.1% to 3% of a CMC by weight of the composition, preferably from 0.5% to 2%, alternatively from 0.6% to 1.8%, alternatively combinations thereof.

In yet another embodiment, the thickener agents may comprise liner sulfated polysaccharide (e.g., carrageenans), CMC, and preferably also a thickening silica for purposes of cost savings while achieving the right balancing of viscosity and elasticity. In one embodiment, the composition comprises a thickener comprising: (a) 0.01% to less than 1.4%, preferably from 0.1% to 1.3%, more preferably from 0.5% to 1.3% of a carrageenan by weight of the oral care composition; and (d) greater than 0.4 wt % to 2 wt %, preferably from 0.5% to 1.8%, more preferably from 0.6% to 1.8% of a carboxymethyl cellulose (CMC) by weight of the oral care composition. In yet another embodiment, the aforementioned thickener further comprises 0.5% to 5%, preferably 1% to 4%, of a thickening silica by weight of the oral care composition.

Low or Free Humectants

The compositions herein may be substantially free or free of humectants, alternatively contain low levels of humectants. The term "humectant," for the present invention, includes edible polyhydric alcohols such as glycerin, sorbitol, xylitol, butylene glycol, propylene glycol, and combinations thereof. In one embodiment, the humectant is selected from sorbitol, glycerin, and combinations thereof. In yet another embodiment, the humectant is sorbitol. In one embodiment, the composition comprises from 0% to less than 20% of humectants by weight of the composition, preferably from 0% to 10%, alternatively from 0% to 5%, alternatively from 0% to 3%, alternatively from 0% to 2%, alternatively from 0% to 1%, alternatively less than 20%, or less than 19%, 18%, 15%, 12%, 8%, 7%, 6%, 4%, 3%, 2%, 1%, or less than 0.5%; or greater than 1%, or greater than 2%, 5%, 10%, or 15%; or combinations thereof, by weight of the composition. In yet another embodiment, the composition contains less than 20% of sorbitol by weight of the composition.

In an alternative embodiment, the compositions of the present invention comprise a humectant, preferably from 1% to 15% by weight of the composition.

Colorant

The oral care compositions herein may include a colorant. Titanium dioxide is one example of a colorant. Titanium dioxide is a white powder which adds opacity to the compositions. Titanium dioxide generally can comprise from about 0.25% to about 5%, by weight of the composition.

Flavorant

The compositions herein may include from about 0.001% to about 5%, alternatively from about 0.01% to about 4%, alternatively from about 0.1% to about 3%, alternatively from about 0.5% to about 2%, alternatively 1% to 1.5%, alternatively 0.5% to 1%, alternatively combinations thereof, of a flavorant composition by weight of the composition. The term flavorant composition is used in the broadest sense to include flavor ingredients, or sensates, or sensate agents, or combinations thereof. Flavor ingredients may include those described in US 2012/0082630 A1 at paragraph 39; and sensates and sensate ingredients may include those described at paragraphs 40-45, incorporated herein by reference. Excluded from the definition of flavorant composition is "sweetener" (as described above).

Examples of flavor compositions or flavor ingredients include: mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, a-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, a-terpineol, linalool, limonene, citral, neral, geranial, geraniol nerol, maltol, ethyl maltol, anethole, dihydroanethole, carvone, menthone, beta-damascenone, ionone, gamma-decalactone, gamma-nonalactone, y-undecalactone, or combinations thereof. Generally suitable flavor ingredients are chemicals with structural features and functional groups that are less prone to redox reactions. These include derivatives of flavor ingredients that are saturated or contain stable aromatic rings or ester groups.

Sensates such as cooling, warming, and tingling agents are useful to deliver signals to the consumer. The most well-known cooling agent is menthol, particularly l-menthol, which is found naturally in peppermint oil. Among synthetic cooling agents, many are derivatives of or are structurally related to menthol, i.e., containing the cyclohexane moiety, and derivatized with functional groups including carboxamide, ketal, ester, ether and alcohol. Examples include the p-menthanecarboxamide compounds such as N-ethyl-p-menthan-3-carboxamide or N-(4-cyanomethylphenyl)-p-menthanecarboxamide (EVERCOOL 180). An example of a synthetic carboxamide cooling agent that is structurally unrelated to menthol is N,2,3-trimethyl-2-isopropylbutanamide. Additional exemplary synthetic cooling agents include alcohol derivatives such as 3-1-menthoxy-propane-1,2-diol, isopulegol, p-menthane-3,8-diol; menthone glycerol acetal; menthyl esters such as menthyl acetate, menthyl acetoacetate, menthyl lactate, and monomenthyl succinate.

Additional agents that are structurally unrelated to menthol but have been reported to have a similar physiological cooling effect include alpha-keto enamine derivatives described in U.S. Pat. No. 6,592,884, including 3-methyl-2-(1-pyrrolidinyl)-2-cyclopenten-1-one (3-MPC), 5-methyl- 2-(1-pyrrolidinyl)-2-cyclopenten-1-one (5-MPC); 2,5-dimethyl-4-(1-pyrrolidinyl)-3(2H)-furanone (DMPF); icilin (also known as AG-3-5, chemical name 142-hydroxyphenyl]-4-[2-nitrophenyl]-1,2,3,6-tetrahydropyrimidine-2-one).

Some examples of warming agents include ethanol; nicotinate esters, such as benzyl nicotinate; polyhydric alcohols; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof.

Examples of some tinging agents include capsaicin; homocapsaicin, jambu oleoresin, zanthoxylum peperitum, saanshool-I, saanshool II, sanshoamide, piperine, piperidine, spilanthol, 4-(1-methoxymethyl)-2-phenyl-1,3-dioxolane, or combinations thereof.

Flavorant Polarity

The polarity of flavorant compositions can be characterized by dielectric constant or water index. Individual flavor ingredients, of the flavor composition, can be characterized by its octanol-water partition coefficient.

Measuring the dielectric constant of a flavorant composition is a convenient way to determine the relative polarity of a mixture of flavor ingredients. The Dielectric Constant (DEC) is measured by placing a charge across two conductive plates with a test liquid between them. These test materials or dielectrics act as insulators which charge the capacitance or charge storage capacity of the circuit. DEC can easily be measured for most liquids by using the Model 870 Dielectric Constant meter produced by Brookhaven. For most liquids used in oral care products the DEC varies from 2 for extremely hydrophobic liquids to 80 for water. Many flavor compositions have DECs from 6 to 11, and individual flavor ingredients can vary from 2 to 22. In general, flavor compositions with the high DEC values solubilize much easier than ones with low values. In general, flavorant compositions are also much easier to emulsify than their individual flavor ingredients (so called "increased mutual solvency"). The DEC of a material is strongly correlated ($R^2$=0.92) to its solubility parameter (SP). SP is a universal parameter used to predict solubility and hydrophobicity of materials. See also "Computation of dielectric constants of solvent mixtures and electrolyte solutions," Wang and Anderko, Fluid Phase Equilibria 186, 103 (2001). In one embodiment, a flavorant composition has a DEC from 1 to 3.5 (i.e., "low polarity"), alternatively a DEC from greater than 3.5 to 8 (i.e., "mid-polarity"), or a DEC from greater than 8, alternatively from greater than 8 to 15 (i.e., "high-polarity"). In another embodiment, the flavorant composition has a DEC from 1 to less than 6, alternatively the flavorant composition has a DEC from 6 to 8, alternatively still the flavorant composition has a DEC from 6 to 11. In yet another embodiment, the flavorant composition has a DEC from 1 to 15, or from 1 to 10, or from 1 to 5, or from 1 to 4, or combinations thereof.

Water number (WN) is another test to measure flavor polarity. Water number is defined as the grams of water needed to achieve permanent turbidity in a solution comprised of 10 grams flavorant composition and 30 grams of 1, 2 hexanediol. In general, water number increases as a function of increasing polarity. Water numbers for most flavor composition vary from around 20 to over 30 grams. In general, values higher than 30 are caused by incorporation of hydrophilic materials such as methyl salicylate, carvone, synthetic Cassia, eugenol, WS 23, MGA, or TK 10. "High Cool Exotic Orange" is an excellent example of a flavorant composition that has a low WN of 7.4 but has a high DEC of 12.6. Without wishing to be bound by theory, the high DEC is due to the presence of coolant agents and the low WN is caused by terpenes. This suggests that this flavorant composition will be more difficult to solubilize than "Cinnamint" that has a WN of 29.7 and a DEC of 12.3.

In one embodiment, a flavorant composition has a WN below 23 (i.e., "low polarity"), alternatively a WN from 1 to 23, or from 1 to 20, or from 1 to 17, or from 1 to 16, or from 1 to 15, or from 1 to 15, or from 15 and below. In another embodiment, the WN is from 23 to 35 (i.e., "mid-polarity"), alternatively a WN from 23 to 40, or from 23 to 30, or from 23 to 29. In yet another embodiment, the WN is greater than 45 (i.e., "high-polarity"), alternatively the WN is greater than 50, or 55, or 60, alternatively the WN is from 45 to more than 200, alternatively from 45 to 200, alternatively from 45 to 79, alternatively combinations thereof. In another embodiment, the flavorant composition has a WN less than 30, alternatively less than 29, or 28, 27, 26, 25, 24, 23, 22, 21, or 21, or at least 1, or 2, 3, alternatively from 1 to 30, or combinations thereof. In yet still another embodiment, the flavorant composition has a WN from 1 to 79, or from 1 to 50, or from 1 to 25.

The individual flavor ingredients (that comprise a flavorant composition) of the present invention may be defined by their octanol/water partition coefficient ("P"). The octanol/water partition coefficient of a flavor ingredient is the ratio between its equilibrium concentrations in octanol and in water. The partition coefficients of flavorant ingredients may more conveniently be given in the form of its logarithm to the base 10, log P. The log P values of many flavorant ingredients have been reported. See, e.g., the Pomona 92 database, available from Daylight Chemical Information Systems, Inc. ("Daylight CIS"), Irvine, Calif. However, the log P values are most conveniently calculated by the Biobyte C log P program contained in Daylight Software version 4.94, also available for license from Daylight CIS. This program also lists experimental log P values when they are available in the Pomona92 database. The calculated log P ("C log P") is determined by the fragment approach of Hansch and Leo (cf., A. Leo, in Comprehensive Medicinal Chemistry, vol. 4, C. Hansch, P. G. Sammens, J. B. Taylor and C. A. Ramsden, Eds., p. 295, Pergamon Press, 1990). The fragment approach is based on the chemical structure of each flavorant ingredient, and takes into account the numbers and types of atoms, the atom connectivity, and chemical bonding. The C log P values, which are the most reliable and widely used estimates for this physicochemical property, are preferably used instead of the experimental log P values in the selection of flavorant ingredients to comprise a flavorant composition.

FIG. 1 provides most of the flavor ingredients from four different flavor compositions, including their weight percentage (relative to the flavor composition), and their C log P value provided according to the method above. The common name and chemical name as well as the CAS number are provided for each flavor ingredient. The four different flavor compositions include a high polarity one identified as "T"; two medium polarity ones identifies as "A" and "W"; and finally a low polarity "C." Not all flavor ingredients are identifiable based on analytical techniques used or are proprietary to supplier.

Generally the more a flavor composition comprises flavor ingredients of a higher C log P value, the more of a negative effect that flavor ingredient has on the overall formulation phase stability. The present invention provides the formulation flexibility to formulate even with those flavor compositions having a relatively large percentage of flavor ingredients having high C log P values. Accordingly, flavor compositions may be characterized by their weight percentage of flavor ingredients having relatively higher C log P values. In one embodiment, the flavor composition comprises at least 50%, alternatively at least 60%, alternatively at least 70% alternatively at least 75%, alternatively from 50% to 90%, alternatively from 60% to 90%, alternatively from 70% to 95%, alternatively from 75% to 85% of flavor ingredient(s) having a C log P of at least 3.06 and higher by weight of the flavor composition, alternatively the flavor ingredient(s) having a C log P from 3.06 to 6, alternatively a C log P from 3.06 to 5, alternatively a C log P from 3.06 to 4.71. In one embodiment, there is 1, 2, 3, 4, 5, 6, 7, or more different flavor ingredients meeting these aforementioned characterizations.

In another embodiment, the flavor composition comprises at least 60%, alternatively at least 70%, alternatively at least 75%, alternatively from 60% to 90%, alternatively from 65% to 95%, alternatively from 70% to 80%, of flavor ingredient(s) having a C log P of at least 4.26 and higher by weight of the flavor composition, alternatively the flavor ingredient(s) having a C log P from 4.26 to 6, alternatively a C log P from 4.26 to 5, alternatively a C log P from 4.26 to 4.71. In one embodiment, there is 1, 2, 3, 4, 5, 6, 7, or more different flavor ingredients meeting these aforementioned characterizations.

In yet another embodiment, the flavor composition comprises at least 50%, alternatively at least 55%, alternatively at least 60%, alternatively at least 65%, alternatively from 50% to 90%, alternatively from 55% to 95%, alternatively from 65% to 85%, alternatively combinations thereof, of flavor ingredients having a C log P of at least 4.38 or higher by weight of the flavor composition, alternatively the flavor ingredient(s) having a C log P from 4.38 to 6, alternatively a C log P from 4.38 to 5, alternatively a C log P from 4.38 to 4.71. In one embodiment, there is 1, 2, 3, 4, 5, 6, 7, or more different flavor ingredients meeting these aforementioned characterizations.

L-menthol is a popular flavor ingredient in many flavor composition for dentifrice formulations. However, at high enough levels in the flavor composition or in the dentifrice composition as a whole, this flavor ingredient may also pose phase stability challenges.

Accordingly, in one embodiment, the flavor composition comprises at least 40%, alternatively at least 45%, alternatively at least 50%, alternatively at least 55%, alternatively at least 60% of L-Menthol by weight of the flavor composition, alternatively the L-Menthol comprises from 40% to 100%, alternatively from 45% to 95%, alternatively from 50% to 90%, alternatively from 55% to 85%, alternatively from 60% to 80%, alternatively combinations thereof, by weight of the composition.

The flavorant composition, of the present invention, may comprise any combination of flavorant ingredients. Four examples of flavor compositions used herein include those of Table 1 indicating their relative polarity and their respective DEC and WN values.

TABLE 1

| Flavorant Composition | Relative Polarity | Dielectric Constant (DEC) | Water Number (WN) |
|---|---|---|---|
| Flavor C | Low | 3.26 | 15 |
| Flavor A | Medium | 5.17 | 23.1 |
| Flavor W | Medium | 5.75 | 24 |
| Flavor T | High | 9.48 | 46 |

FIG. 1 provides most of the flavor ingredients for Flavors C, A, W, and T, including their weight percentage (relative to the flavor composition). A summary is provided:

Flavor C is a flavorant composition comprising the following components and weight percentages relative to the flavorant composition: d-limonene (56%); ANETHOLE (11%); beta-pinene (9%); L-menthol (4%).

Flavor A is a flavorant composition comprising the following components and weight percentages relative to the flavorant composition: L-Menthol (51%); ANETHOLE (11%); EUCALYPTOL (14%); and 1-Menthone (11.5%).

Flavor W is a flavorant composition comprising the following component and weight percentages relative to the flavorant composition: L-Menthol (56%); WS-3 (4%); ANETHOLE (4%); EUCALYPTOL (4%); Methyl Salicylate (20%).

Flavor T is a flavorant composition comprising the following component and relative weight percentages relative to the flavorant composition: L-Menthol (60%); WS-3 (4%); EUCALYPTOL (11%); propylene glycol (19%).

Examples

The following examples and descriptions further clarify embodiments within the scope of the present invention. These examples are given solely for the purpose of illustration and are not to be construed as limitations of the present invention as many variations thereof are possible without departing from the spirit and scope.

TABLE 2

| | Weight Percentage in Formula Examples: | | | | |
|---|---|---|---|---|---|
| INGREDIENTS: | A | B | C | D | E |
| USP Water | 57.05 | 56.05 | 56.25 | 56.55 | 55.55 |
| Calcium Carbonate | 32 | 32 | 32 | 32 | 32 |
| Silica Thickening Dental Type NF | 2.6 | 2.6 | 2.6 | 2.6 | 2.6 |
| Carrageenan | 1.2 | 1.2 | 1.2 | 1.2 | 1.2 |
| Sodium Monoflourophosphate | 1.1 | 1.1 | 1.1 | 1.1 | 1.1 |
| Sodium Carboxymethyl Cellulose | 0.9 | 0.9 | 0.9 | 0.9 | 0.9 |
| Sodium pyrophosphate tetrabasic | 0.6 | 0.6 | 0.6 | 0.6 | 0.6 |
| Sodium Lauryl Sulfate | 1.1 | 2.1 | 1.6 | 1.1 | 2.1 |
| Flavor* | 0.7 | 0.7 | 1 | 1.2 | 1.2 |
| PEG† | 2 | 2 | 2 | 2 | 2 |
| Tribasic Sodium Phosphate Dodecahydrate | 0.42 | 0.42 | 0.42 | 0.42 | 0.42 |
| Saccharin Sodium, USP | 0.25 | 0.25 | 0.25 | 0.25 | 0.25 |
| Sodium Phosphate Monobasic Monohydrate | 0.08 | 0.08 | 0.08 | 0.08 | 0.08 |

*Flavor is a low polarity flavorant composition (Flavor C); a medium polarity flavorant composition (Flavor A); or a high polarity flavorant composition (Flavor T). See FIG. 1.
†PEG can be either PEG 300, PEG 400, PEG 600, PEG 1000, or PEG 1300-1600 (mixture).

Data

FIG. 2 is a table detailing the components of formulation Examples 1-15 that are various toothpaste formulations that vary on the amount of surfactant (i.e., sodium lauryl sulfate or "SLS"), and the polarity type of flavorant composition and the amount thereof. The low polarity flavorant composition is "Flavor C"; the medium polarity flavorant composition is "Flavor A"; and the high polarity flavorant composition is "Flavor T". See Tables 1, 2, 3 and FIG. 1 herein for more details about these flavorant compositions. Control compositions did not contain any PEG. Experimental compositions all contained 2 weight percent of PEG of varying molecular weights. Specifically, PEG 300, PEG 400, PEG 600, PEG 1000, and PEG 1300-1600 are tested (substituted for USP water in the control compositions to yield 100 wt % of total ingredients). Those formulations that are phase unstable at 6 months are indicated by a negative sign, while those formulations that are phase stable at 6 months are indicated by a positive sign. Generally, those formulations having PEG are stable while many control compositions without PEG are unstable after 6 months.

Referring to the control formulations of Examples 1-5, these all contain the low polarity flavorant composition at varying levels. The amount of SLSS also varied. These compositions all become phase unstable within 6 months. Notably, even Example 2 having a relatively high level of surfactant and low amount of flavorant composition failed. Corresponding experimental formulations have 2 weight percent of PEG of varying molecular weight demonstrate that these formulations all are phase stable after 6 months under ambient conditions.

Referring to Examples 6-15, these contain flavorant compositions at medium and high polarity (vs. low) and also varying amounts of SLSS surfactant. Generally, there are some formulations that are phase stable after 6 months without PEG (Examples 6, 8, 10, 11, and 14), while other formulations that are phase unstable (Examples 7, 9, 12, 13, and 15). Comparing to Examples 1-5, this suggests that those formulations having low polarity flavorant are generally more challenging to keep phase stable than those having medium and high polarity flavorants (since all of the control formulations of the low polarity flavorant compositions failed to be phase stable). Turning to the experiment formulations of Example 6-15, those formulations have 2 weight percent PEG having molecular weight of PEG 400 and higher all resulted in phase stable compositions. However, only some of the otherwise unstable formulation having PEG 300 became stable (specifically Examples 9 and 13), while those formulations of Examples 7 and 12 required a PEG having a molecular weight of at least PEG-400 to become stable.

Generally this data indicates that incorporating PEG into otherwise phase unstable formations will improve the phase stability. Generally, those PEGs having molecular weight higher than PEG 300 may provide even better results with respect to phase stability.

Figure 3B:
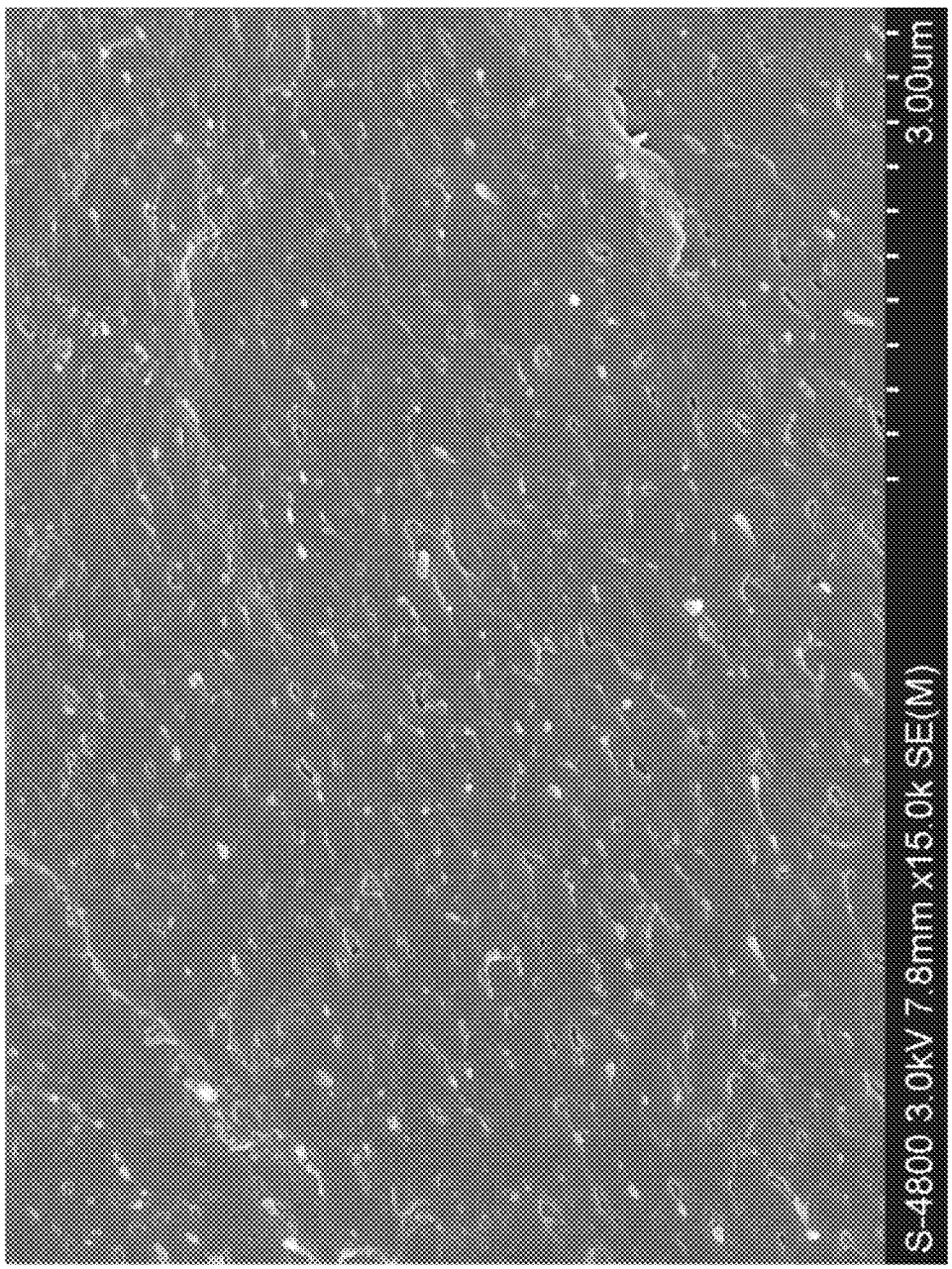

FIG. 3 are Scanning Electron Microscopy (SEM) images of phase unstable compositions (FIG. 3A) and a phase stable composition (FIG. 3B). Both compositions of FIGS. 3A and 3B are aged for four months under ambient conditions. The unstable composition of FIG. 3A is 1% of Flavorant A (medium polarity flavorant composition) and 2.1% sodium lauryl sulfate by weight of the unstable composition, and wherein the remaining component of the composition is water. The stable composition of FIG. 3B is similarly 1% of Flavorant A, 2.1% sodium lauryl sulfate, and 2% of polyethylene glycol-300 (i.e., PEG having a range of average molecular weight from 285 to 315 Daltons), by weight of the stable composition, and wherein the remaining component of the composition is water. Both SEM images of FIG. 3 are magnified at 10,000× and all are taken with the same instrument (e.g., SEM Hitachi S-4800) and under the same critical operating parameters (e.g., accelerated voltage (3 kV)). The reduction in emulsion size of FIG. 3B suggests, without wishing to be bound by theory, that PEG is improving the solubility of the SLS in matrix.

Table 3 compares the phase stability between two formulations only differing in that one contains 2% by weight of the composition of PEG-300 while the other does not. Examples 16 and 17 provided in Table 4 below notably all have 2.1 wt % of surfactant Sodium Lauryl Sulfate, 1 wt % Flavor A—medium polarity flavorant composition. The experimental formulation having 2 wt % PEG-300 is stable after 4 months under ambient conditions while the control formulation is not.

TABLE 3

| INGREDIENTS: | Percentage in Formula Examples: | |
|---|---|---|
| | 16 | 17 |
| Water | 94.45 | 92.45 |
| Sodium Monoflourophosphate | 1.1 | 1.1 |
| Sodium pyrophosphate tetrabasic | 0.6 | 0.6 |
| Sodium Lauryl Sulfate | 2.1 | 2.1 |
| Flavor A- Medium Polarity Flavorant Comp. | 1 | 1 |
| PEG-300 | 0 | 2 |
| Tribasic Sodium Phosphate Dodecahydrate | 0.42 | 0.42 |
| Saccharin Sodium, USP | 0.25 | 0.25 |
| Sodium Phosphate Monobasic Monohydrate | 0.08 | 0.08 |
| Phase Stability After 4 Months Under Ambient Conditions: | No | Yes |
| FIG.: | 3A | 3B |

Figure 4:
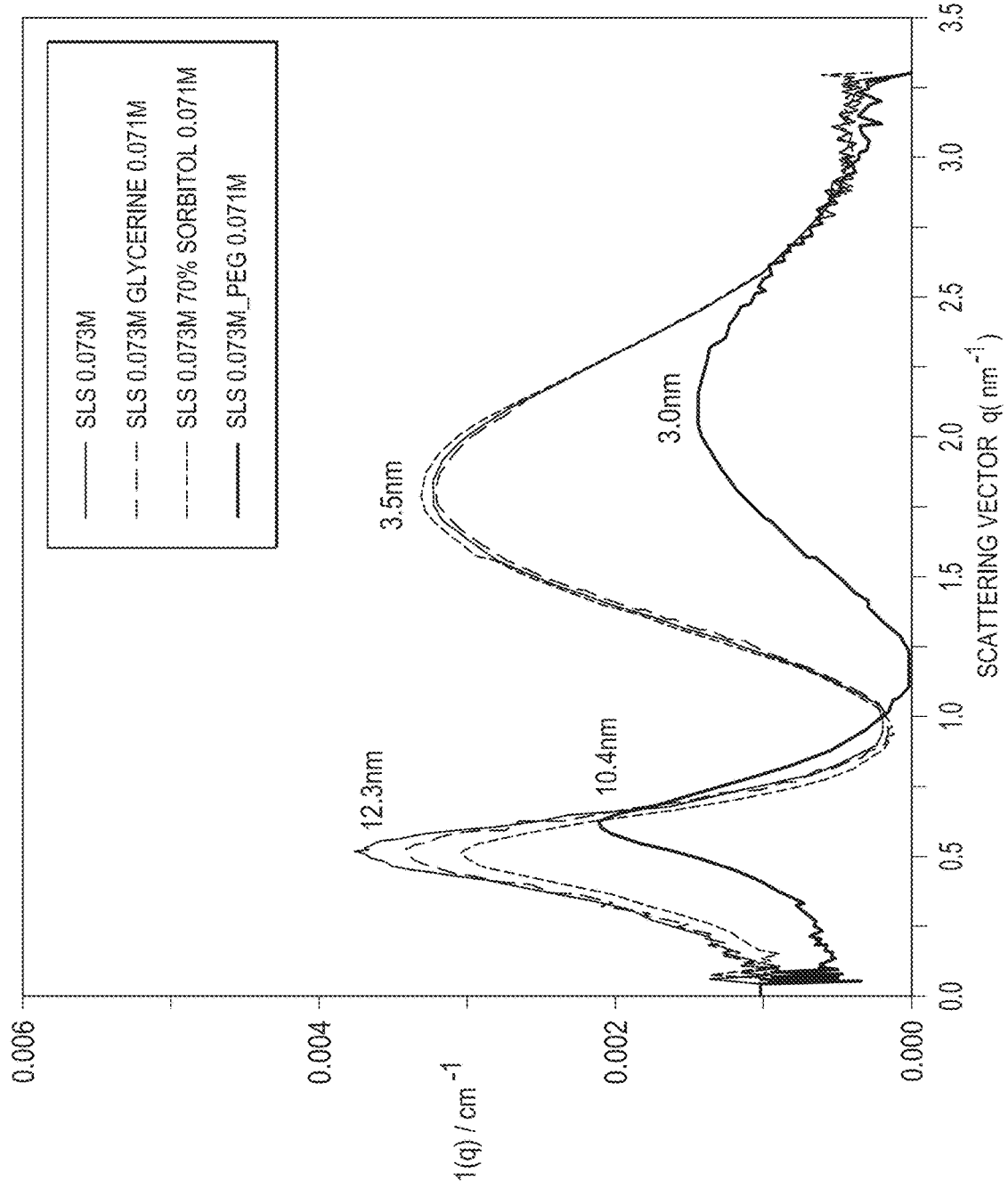
FIG. 4 is a synchrotron data comparing micelle spacing and micelle size between four formulations.

FIG. 4 is a synchrotron experiment demonstrating the superior effect of PEG in the dissolution of surfactant Sodium Lauryl Sulfate ("SLS") evidenced by the reduced size of the SLSS micelle as compared to humectants glycerine and sorbitol. A control solution and four experimental solutions are prepared and evaluated by synchrotron. SLS water solution at a concentration at 0.073 mol/L (i.e., 2.1 wt %) is prepared as control. A SLS solution (0.073 mol/L) with humectant Glycerin at 0.071 mol/L is prepared, and analogous SLS solutions of humectant Sorbitol (0.071 mol/L) and PEG-300 (0.071 mol/L) are prepared (substituting for glycerin). The solution of PEG-300 is a 2 wt % at this mol/L concentration. Turning to FIG. 4 and the synchrotron spectrum, there is no material difference in terms of SLSS micelles between the SLSS control solution and those samples with glycerin and sorbitol. In contrast, the micelle size of sample with PEG-300 is significantly reduced thereby indicating increased dissolution of surfactant SLS as compared to the control and humectant samples.

The SAXS measurements are performed at ID02 beamline at the European Synchrotron Radiation Facility (ESRF) in Grenoble, France. Exposure time is set at 10 ms to ensure good signal and minimize radiation damage effects with higher flux ($10^{14}$ photons/s) to the CCD. A fast read-out, low-noise CCD detector (FReLoN Kodak CCD, 100 mm×100 mm) is placed 1.2 meters away from the sample. The wavelength of the incident beam ($\lambda$) is 0.0995 nm, allowing the q ranges of 0.06-4.0 $nm^{-1}$, where q is the magnitude of the scattering vector ($q=(4\pi/\lambda)\sin\theta$, where $2\theta$ is the scattering angle).

Table 4 below summarizes the superior phase stability effects of PEG600 over 3 months and 5 months (at various concentrations), under ambient conditions, as compared to PEG of different molecular weights (both higher and lower molecular weights) and at various concentrations while holding the concentration of flavorant composition and anionic surfactant constant. All samples notable contain Flavorant A at 0.85 weight percent, and anionic surfactant Sodium Lauryl Sulfate at 2.1% weight percentage of the formulation. Other ingredients of the formulations are shown in the FIG. 2.

TABLE 4

Comparative Phase Stability between molecular weights of PEG over time. Phase stability is indicated with a plus sign ("+") while phase instability is indicated with a negative sign ("−").

| PEG molecular weight and (weight percentage) | Phase Stability 3 Months | Phase Stability 5 Months |
|---|---|---|
| PEG 400 (4 wt %) | + | + |
| PEG 400 (8 wt %) | + | + |
| PEG 400 (10 wt %) | + | + |
| PEG 600 (4 wt %) | + | + |
| PEG 600 (8 wt %) | + | + |
| PEG 600 (10 wt %) | + | + |
| PEG 1000 (4 wt %) | −/+ [1] | − |
| PEG 1000 (8 wt %) | − | − |
| PEG 1000 (10 wt %) | − | − |
| PEG 1300-1600 (4 wt %) | + | + |
| PEG 1300-1600 (8 wt %) | − | − |
| PEG 1300-1600 (10 wt %) | − | − |

[1] Bubbles are visible suggesting beginning stages of phase instability.

Without wishing to bond by theory, PEG-600 likely strikes the best balance between being completely soluble in water and yet non-polar enough (given its size) to act as an effective emollient for the flavor ingredient(s) oil droplets. Accordingly, one preferred PEG is having a range of average molecular weight from 500 to 700 Daltons, alternatively from 550 to 650 Daltons.

Method of Use

The present invention also relates to methods for cleaning and polishing teeth. The method of use herein comprises contacting a subject's dental enamel surfaces and oral mucosa with the oral compositions according to the present invention. The method of treatment may be by brushing with a dentifrice or rinsing with a dentifrice slurry or mouthrinse. Other methods include contacting the topical oral gel, mouthspray, toothpaste, dentifrice, tooth gel, tooth powders, tablets, subgingival gel, foam, mousse, chewing gum, lipstick, sponge, floss, petrolatum gel, or denture product or other form with the subject's teeth and oral mucosa. Depending on the embodiment, the oral composition may be used as frequently as toothpaste, or may be used less often, for example, weekly, or used by a professional in the form of a prophy paste or other intensive treatment.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:
   (a) 50% to 70% of water by weight of the composition;
   (b) 25% to 60% of a calcium-containing abrasive by weight of the composition;
   (c) 0.1% to 4% of a polyethylene glycol (PEG) 900 to PEG 1300 by weight of the composition; and
   (d) 0.001% to 5% of a flavorant composition by weight of the dentifrice composition, wherein the flavorant composition has a Dielectric Constant (DEC) from 1 to 15; and
   wherein the flavorant composition has a Water Number (WN) from 1 to 50;
   wherein the composition comprises less than 0.5% of a humectant, by weight of the composition, the composition does not phase separate after four months under ambient conditions, and the pH is greater than 9.

2. The composition of claim 1, wherein the humectant is selected from the group consisting of glycerin, sorbitol, xylitol, butylene glycol, propylene glycol, and combinations thereof.

3. The composition of claim 1, wherein the flavorant composition is comprised of flavor ingredients wherein at least 50%, of the flavor ingredient(s) by weight of the flavorant composition having a C log P value of at least 3.06 and higher.

4. The composition of claim 3, wherein the flavorant composition is comprised of flavor ingredients wherein at least 60% of the flavor ingredient(s) by weight of the flavorant composition having a C log P value of at least 4.26 and higher.

5. The composition of claim 4, wherein the flavorant composition is comprised of flavor ingredients wherein at least 50% of the flavor ingredient(s) by weight of the flavorant composition having a C log P value of at least 4.26 and higher.

6. The composition of claim 1, wherein the flavorant composition comprises at least 40% of L-menthol as a flavorant ingredient by weight of the flavorant composition.

7. The composition of claim 1, further comprising a fluoride ion source.

8. The composition of claim 1, further comprising 0.1% to 5% of sodium lauryl sulfate by weight of the composition.

9. A method of treating tooth enamel comprising the step of brushing teeth with the dentifrice composition of claim 8.

10. The composition of claim 1, wherein the composition comprises 0.1% to 3% of a polyethylene glycol (PEG) 900 to PEG 1300 by weight of the composition.

11. A dentifrice composition comprising:
   (a) 50% to 70% of water by weight of the composition;
   (b) 25% to 40% of a calcium-containing abrasive by weight of the composition;
   (c) 0.1% to 4% of a polyethylene glycol (PEG) 900 to PEG 1300 by weight of the composition;
   (d) 0.001% to 5% of a flavorant composition by weight of the dentifrice composition wherein the flavorant composition has a Dielectric Constant (DEC) from 1 to 15; and wherein the flavorant composition has a Water Number (WN) from 1 to 50;

wherein the composition less than 1% of a humectant, by weight of the composition, the composition does not phase separate after four months under ambient conditions, and the pH is greater than 9.

* * * * *